(12) United States Patent
Sieber et al.

(10) Patent No.: US 6,177,009 B1
(45) Date of Patent: Jan. 23, 2001

(54) APPARATUS FOR TREATING BIOMOLECULES

(75) Inventors: Manfred Sieber, Niedeggen; Robert Zeidler, Kreuzau-Drove, both of (DE)

(73) Assignee: Macherey, Nagel GmbH & Co., Handelsgesellschaft (DE)

( * ) Notice: Under 35 U.S.C. 154(b), the term of this patent shall be extended for 0 days.

(21) Appl. No.: 09/262,012

(22) Filed: Mar. 4, 1999

(30) Foreign Application Priority Data

Apr. 3, 1998 (DE) .......................................... 298 30 712 U

(51) Int. Cl.[7] .................................................... B01D 15/08
(52) U.S. Cl. ...................... 210/198.2; 210/657; 422/70; 422/101; 436/178
(58) Field of Search ................................... 210/656, 657, 210/198.2, 282; 422/69, 70, 101, 102; 436/161, 177, 178

(56) References Cited

U.S. PATENT DOCUMENTS

| | | | |
|---|---|---|---|
| 4,238,196 | * 12/1980 | Acuff | 210/656 |
| 4,243,534 | * 1/1981 | Bulbenko | 210/198.2 |
| 4,270,921 | * 6/1981 | Graas | 210/198.2 |
| 4,341,635 | * 7/1982 | Golias | 210/198.2 |
| 4,787,971 | 11/1988 | Donald | 210/198.2 |
| 4,832,916 | 5/1989 | Gilak | 422/70 |
| 4,956,298 | 9/1990 | Diekmann | 430/311 |
| 5,578,459 | 11/1996 | Gordon et al. | 135/29 |

FOREIGN PATENT DOCUMENTS

| | | | |
|---|---|---|---|
| 3843610 | 7/1989 | (DE) | 210/198.2 |
| 3913814 | 7/1990 | (DE) | 210/198.2 |
| 4208732 | 9/1993 | (DE) | 210/198.2 |
| 195 12 361 | 10/1996 | (DE) | 210/198.2 |
| 29803712 | 6/1998 | (DE) | 210/198.2 |
| 0738733 | 10/1993 | (EP) | 210/198.2 |
| 0588564 | 3/1994 | (EP) | 210/198.2 |
| 0616638 | 9/1994 | (EP) | 210/198.2 |
| 2558847 | of 1985 | (FR) | 210/198.2 |
| 93/11218 | 6/1993 | (WO) | 210/198.2 |
| 95/02049 | 1/1995 | (WO) | 210/198.2 |
| 95/18851 | 7/1995 | (WO) | 210/198.2 |
| 96/41810 | 12/1996 | (WO) | 210/198.2 |

OTHER PUBLICATIONS

Sartorius Membranfilter pp. 1–3 Undated.
Quigen Product Guide 1996, pp. 27, 28, 32, 48, 49, 50, 56, 57, 72, & 75.
Quigen News for Biochemistry and Molecular Biology, "MRNA Without. . ." Feb. 1994 pp. 1–16.
Quiegen News for Biochemistry and Molecular Biology, "High Performance Sequencing Templates. . ." Jan. 1994 p. 1–20.
Quigen News for Biochemistry and Molecular Biology, "The QIAprep–spin Plasmid Kit for . . ." Jan. 1993 pp. 1–12.
Biosolutions, Application and Product News for Lab Researchers, vol. 12, 2, Apr. 1994, pp. 1–8.

* cited by examiner

Primary Examiner—Ernest G. Therkorn
(74) Attorney, Agent, or Firm—Liniak, Berenato, Longacre & White, LLC

(57) ABSTRACT

Disclosed is an apparatus for isolating nucleic acids having a separation column which has a top inlet and a bottom outlet in which a separation device is arranged, and having a collection vessel for collecting liquid emerging from the outlet. The ratio between the internal volume of the separation column above the separation device and the surface area of the separation device is at least 10 ml/cm$^2$.

24 Claims, 1 Drawing Sheet

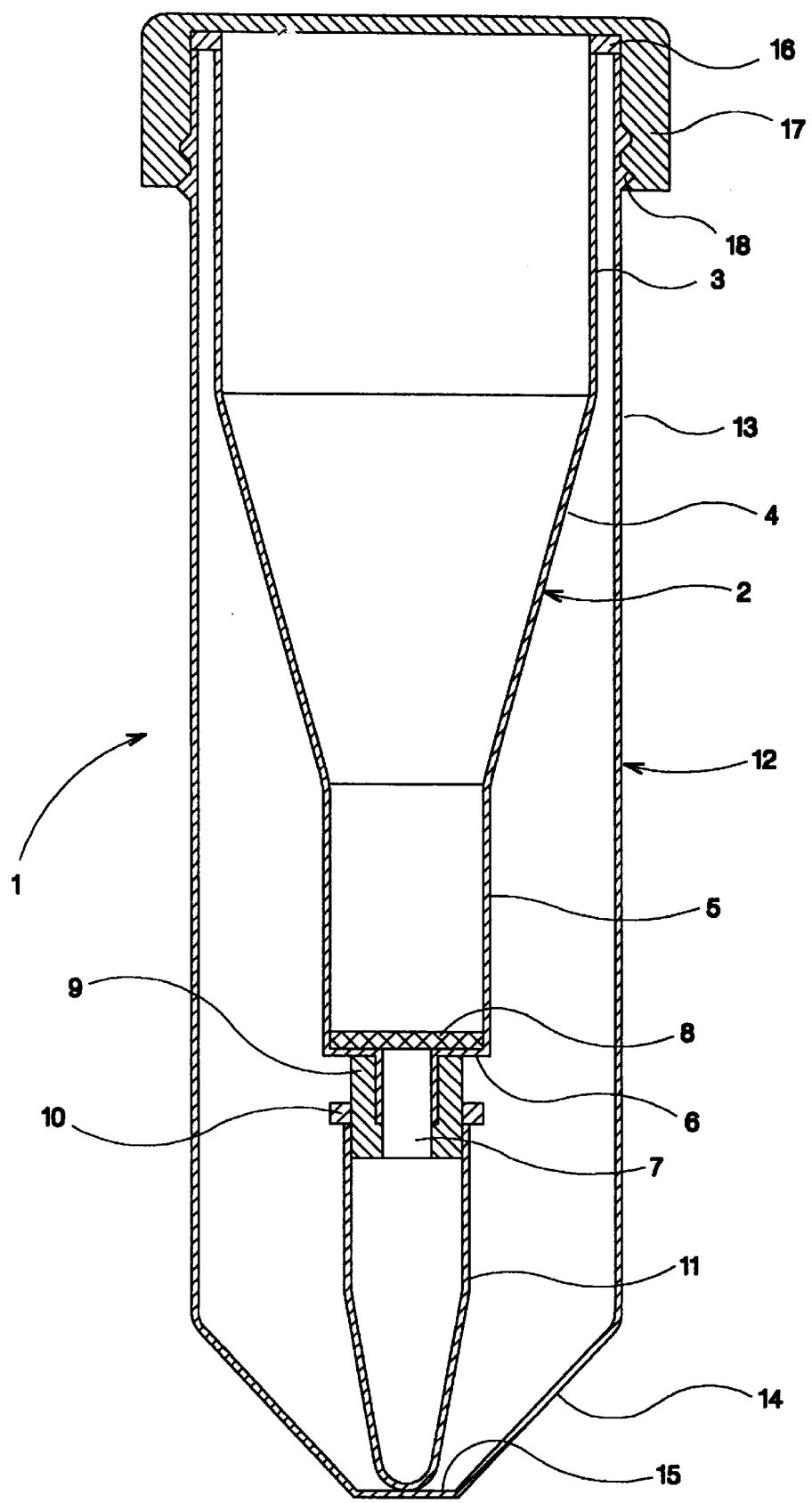

APPARATUS FOR TREATING BIOMOLECULES

The invention concerns an apparatus for treating biomolecules, in particular for isolating nucleic acids having a separation column which has a top-end inlet and a bottom-end outlet and in which a separation device is arranged, and having a collection vessel for collecting the liquid emerging from the outlet.

The detection of viral nucleic acids is becoming increasingly important in many areas of molecular medicine and diagnostics. Improved therapeutic strategies make it necessary to track viral titer (e.g. for HIV) down to very low values. Blood samples and blood donations must be examined with regard to their viral load, the result being to create a very large sample volume. In order to reduce both complexity and sample numbers, samples are combined so that, for example, ten samples can be examined together. This makes it necessary, inter alia, to develop apparatuses and methods with which larger sample volumes can be processed but with which even small viral loads can nevertheless be detected. A similar problem arises in the isolation of DNA quantities from biological fluids, for example urine, body fluids, etc.

Further possible applications are the specific binding and isolation of proteins or peptides which occur in low concentrations in biological matrices, e.g. serum, and must be detected.

EP 0 616 638 B1 and DE 38 43 610 A1 disclose apparatuses which comprise a separation column and a collection vessel. The separation column has a top-end inlet for admitting the sample, and a bottom-end outlet which projects into the collection vessel. A separation device, for example in the form of single- or multi-stage filters, is located in the lower region of the separation column. The separation device is configured so that the biomolecules to be recovered are bound adsorptively to the separation column. If constituents of, for example, cell material are to be recovered, this is usually preceded by several digestion and purification steps. After isolation, the biomolecules are detached from the separation device using an eluate, and collected in a separate collection vessel. They are then available for further examination.

With the known apparatuses, relatively large elution volumes are necessary in order to release the isolated biomolecules. The concentration of the biomolecules in the eluate is correspondingly low. Since only comparatively small volumes can be used in the subsequent detection methods, the analysis of small quantities of biomolecules, for example nucleic acids, presents considerable difficulties.

Attempts have therefore been made to perform a concentration operation by way of ultracentrifuging or ultrafiltration. These methods have not, however, proven particularly successful, since they are poorly reproducible and moreover require a considerable outlay in terms of equipment and tine.

It is the object of the invention to configure an apparatus of the kind cited initially in such a way that without a separate concentration step, a substantially smaller elution volume is sufficient even for large sample volumes. At the same time, cross-contamination is to be reliably prevented.

According to the present invention, this object is achieved in that the ratio between the internal volume of the separation column above the separation device and the surface area of the separation device is at least 10 ml/cm$^2$, preferably at least 30 ml/cm$^2$; and that a collection vessel is present into which the separation column and the collection vessel joined thereto can be inserted. This can be an ordinary centrifuging vessel having a top-end opening and a shoulder for the receptacle in a centrifuge. It has been found that with this separation column geometry, substantially smaller elution volumes are needed in order to release the purified biomolecules out of the separation device. The volume ratio between sample and eluate is at least 8 and can reach 100. The result is thus a concentration of the biomolecules in the eluate, which eliminates the need for previous or subsequent concentration steps even when the biomolecule concentration in the sample is low, and makes subsequent analysis much easier and more reliable. The external vessel offers a high level of protection against cross-contamination, and serves moreover as a collection vessel when the biomolecules from the sample are being bound to the separation device, and during subsequent washing steps. Comparatively large volumes occur in this context, which can be received by the external vessel. Because of the geometry according to the present invention and the resulting small quantity of eluate, a comparatively small collection vessel can then be used for elution of the purified biomolecules.

In a development of the invention, provision is made for the surface area of the separation device to be less than 0.4 cm$^2$, preferably less than 0.3 cm$^2$, for an internal volume of at least 15 ml, preferably 20 ml.

The geometry according to the present invention can, in principle, also be attained with cylindrical separation columns. In order for the separation column to be compact, however, it is more advantageous for the internal cross section of the separation column to increase from the separation device toward the inlet, for example constituting a fimnel segment. Cylindrical segments can respectively adjoin the funnel segment at the top and/or bottom end. The separation device should be supported on a shoulder which causes the cross section of the outlet to taper.

In a particularly preferred embodiment, the apparatus has an external vessel into which the separation column and the collection vessel joined thereto can be inserted. This can be an ordinary centrifuging vessel having a top-end opening and a shoulder for the receptacle in a centrifuge. The external vessel offers a high level of protection against cross-contamination, and serves moreover as a collection vessel when the biomolecules from the sample are being bound to the separation device, and during subsequent washing steps. Comparatively large volumes occur in this context, which can be received by the external vessel. Because of the geometry according to the present invention and the resulting small quantity of eluate, a comparatively small collection vessel can then be used for elution of the purified biomolecules. Preferably the external vessel is dimensioned so that the separation column and the collection vessel joined thereto fit substantially completely into the external vessel. The external vessel should have a length which corresponds to the length of the separation column and of the collection vessel joined thereto, and both are held immovably in the external vessel so that changes in position do not occur during centrifuging.

The external vessel should advantageously have a cap in order to enclose the separation column and collection vessel completely and thus form a barrier against cross-contamination. In order to prevent independent movement of the separation column, it is further advantageous if the separation column and the collection vessel joined thereto can be clamped between the cap and the base of the external vessel. The same purpose is served if the separation column has an annular flange, overlapping the upper rim of the external vessel, which can be clamped between the cap and external vessel and thus functions as a seal.

Provision is further made, according to the invention, for the collection vessel to be joinable in airtight fashion to the separation column in order to prevent any leakage of the collected substance. The collection vessel can be configured so as to be slid onto the outlet of the separation column; an adapter can also be interposed for this purpose.

It is understood that the collection vessel is to be closable by way of a cover so that the eluate containing the biomolecules can be safely transported and stored. For this purpose, the cover can be joined in known fashion to the collection vessel by a tape.

BRIEF DESCRIPTION OF THE DRAWING

The sole FIGURE shows apparatus for treating biomolecules according to the invention.

DESCRIPTION OF THE PREFERRED EMBODIMENTS

The drawing illustrates the invention in more detail with reference to an exemplifying embodiment. It shows an apparatus 1 for the isolation of viral nucleic acids.

Apparatus 1 has a separation column 2 made of a plastic material, which has an upper cylindrical segment 3, a frustoconical funnel segment 4 adjacent thereto, and a lower cylindrical segment 5 which terminates in an annular shoulder 6 adjoining which is a cylindrical outlet 7.

A filter disk 8, which is configured in accordance with the biomolecules to be isolated, rests on annular shoulder 6. The filters disclosed in EP 0 616 638 B1 are suitable, for example, for this purpose.

An adapter sleeve 9 is slid onto outlet 7. A small-volume collection vessel 11, equipped with an upper rim 10, is placed onto adapter sleeve 9, the contact of the inner side of collection vessel 11 against the outer side of adapter sleeve 9 being airtight.

The unit made up of separation column 2 and collection vessel 11 is placed into a centrifuging vessel 12. Centrifuging vessel 12 has substantially a cylindrical wall 13 which terminates at the bottom end in a conical segment 15 with base 15. Collection vessel 11 rests on base 15. An annular flange 16, which forms the upper rim of separation column 2, sits on the upper rim of collection vessel 11. The upper sides of centrifuging vessel 12 and separation column 2 are closed off by a hat-shaped cap 17 which grips annular flange 16 and is joined via threads 18 to centrifuging vessel 12.

Using apparatus 1 described above, viral nucleic acids can be recovered as follows:

Two milliliters of a serum or plasma sample are added to several (usually two to four) times that volume of LP1 lysis buffer (in this case 4 ml LP1: 4.5 M guanidine thiocyanate [GTC], 20 mM TRIS/HCl, pH 6.5; 20 mM EDTA, pH 8.0; 1% Triton×100). The mixture is pipetted in and out several times, vortex-mixed, and incubated for several minutes at room temperature. If the lysis mixture exhibits visible particles and/or turbidity, it must be centrifuged for 5 to 10 minutes in order to remove solids which might clog the membrane. If the expected quantities of nucleic acid are very small, nonspecific RNA ("carrier RNA"; e.g. poly(A)) must be added to the lysis buffer in order to increase the yield.

Advantageously, a comparable quantity (in this case 4 ml; final concentration 5–50%) of ethanol (>98%), isopropanol, or acetone is added to the clear lysate, and again thoroughly vortex-mixed. The mixture can then be introduced into separation column 2. Separation column 2 is then placed into a 50-ml centrifuging vessel 12. The sample is then centrifuged for 3 minutes at a speed of 1500 rpm. The solution passes through filter disk 8, while nucleic acids are bound. The filtrate is collected in centrifuging vessel 12.

Separation column 2 is then filled with several milliliters of washing buffer WP1 (in this case 3 ml WP1: 80% 1.5 M GTC; 30 mM sodium citrate, pH 7.2; 20% ethanol). The centrifuging step as described above is repeated, and the filtrate is discarded. The result of the washing steps with ethanol-containing WP1 and other washing buffers is principally to remove undesirable contaminants from filter disk 8, while the viral nucleic acids remain bound.

Separation column 2 is then filled with washing buffer WP2 (20 mM TRIS/HCl, pH 7.5; 50 mM NaCl; 80% ethanol). The centrifuging step is performed as described above, the filtrate is discarded, and the washing process is repeated again in the same fashion. The result of the washing steps using washing buffer WP2, with its high level of ethanol, is principally to wash the chaotropic salts of the lysis buffer out of filter disk 8.

Prior to elution, a further washing step with acetone can optionally be performed in order to remove traces of ethanol. Many amplification procedures performed subsequently contain ethanol-sensitive enzymes, so that the detection of viral nucleic acids is inhibited, or even entirely prevented, in the presence of ethanol.

Separation column 2 is then centrifuged empty for a further 10 minutes at 3000–5000 rpm in order to remove washing buffer residues or acetone residues. For complete drying, separation column 2 can then be held for another 5–10 minutes at room temperature or at 37EC.

Prior to elution, separation column 2 is transferred into a fresh, sterile 50-ml centrifuging vessel 12, a 500-ul collection vessel 11 having first been placed in airtight fashion on lower outlet 7 by way of adapter sleeve 9. 100 ul of RNase-free water (preconditioned to 60EC) is then pipetted directly onto filter disk 8 and allowed to incubate for 1 minute. Centrifuging for 3 minutes at 3000 rpm causes the elution fraction containing the viral nucleic acids to be transferred into collection vessel 11 located beneath the separation column. Said vessel is pulled off separation column 2 to allow storage of the sample, and closed off with a cover (not depicted here).

What is claimed is:

1. An apparatus (1) for treating biomolecules, having a separation column (2) which has a top-end inlet and a bottom-end outlet (7) and in which a separation device (8) is arranged, and having a collection vessel (11) for collecting the liquid emerging from the outlet (7), wherein the ratio between the internal volume of the separation column (2) above the separation device (8) and the surface area of the separation device (8) is at least 10 ml/cm$^2$; and an external vessel (12) is present into which the separation column (2) and the collection vessel (11) joined thereto can be inserted.

2. The apparatus as defined in claim 1, wherein the ratio is at least 30 ml/cm$^2$.

3. The apparatus as defined in claim 1, wherein the surface area of the separation device (8) is less than 0.4 cm$^2$.

4. The apparatus as defined in claim 1, wherein the internal volume of the separation column (2) is at least 15 ml.

5. The apparatus as defined in claim 1, wherein the internal cross section of the separation column (2) increases from the separation device (8) toward the inlet.

6. The apparatus as defined in claim 5, wherein the separation column (2) has a funnel segment (4) between the inlet and separation device (8).

7. The apparatus as defined in claim 6, wherein a cylindrical segment (3, 5) respectively adjoins the funnel segment (4) at the top and/or bottom end.

8. The apparatus as defined in claim 1, wherein the separation device (8) is supported on a shoulder (6) which causes the cross section of the outlet (7) to taper.

9. The apparatus as defined in claim 1, wherein the separation column (2) and the collection vessel (11) joined thereto fit substantially completely into the external vessel (12).

10. The apparatus as defined in claim 9, wherein the external vessel (12) has a length which corresponds to the length of the separation column (2) and of the collection vessel joined thereto (11).

11. The apparatus as defined in claim 9, wherein the separation column (2) and the collection vessel (11) joined thereto are held immovably in the external vessel (12).

12. The apparatus as defined in claim 1, wherein the external vessel (12) has a cap (17).

13. The apparatus as defined in claim 12, wherein the cap (17) is of hat-shaped configuration, an annular flange, acting as projection, covering the upper end region of the external vessel (12).

14. The apparatus as defined in claim 1, wherein the separation column (2) and the collection vessel (11) joined thereto can be clamped between the cap (17) and the base (15) of the external vessel (12).

15. The apparatus as defined in claim 1, wherein the separation column (2) has an annular flange (16) overlapping the upper rim of the external vessel (12).

16. The apparatus as defined in claim 1, wherein the collection vessel (11) is joinable in airtight fashion to the separation column (2).

17. The apparatus as defined in claim 1, wherein the collection vessel (11) can be slid onto the outlet (7) of the separation column (2).

18. The apparatus as defined in claim 17, wherein an adapter (9) which fits the collection vessel (11) is placed on the outlet (7) of the separation column (2).

19. The apparatus as defined in claim 1, wherein the collection vessel (11) is closable by way of a cover.

20. The apparatus as defined in claim 19, wherein the cover is joined to the collection vessel (11) by a tape.

21. The apparatus as defined in claim 1, wherein the treatment of biomolecules is the isolation of nucleic acids.

22. The apparatus as defined in claim 1, wherein the ratio is more than 70 ml/cm$^2$.

23. The apparatus as defined in claim 1, wherein the surface area of the separation device (8) is less than 0.3 cm$^2$.

24. The apparatus as defined in claim 1, wherein the internal volume of the separation column (2) is at least 20 ml.

* * * * *